(12) United States Patent
Slayton et al.

(10) Patent No.: US 7,142,905 B2
(45) Date of Patent: *Nov. 28, 2006

(54) VISUAL IMAGING SYSTEM FOR ULTRASONIC PROBE

(75) Inventors: Michael H. Slayton, Tempe, AZ (US); Peter G. Barthe, Phoenix, AZ (US)

(73) Assignee: Guided Therapy Systems, Inc., Mesa, AZ (US)

( * ) Notice: Subject to any disclaimer, the term of this patent is extended or adjusted under 35 U.S.C. 154(b) by 157 days.

This patent is subject to a terminal disclaimer.

(21) Appl. No.: 10/358,110

(22) Filed: Feb. 4, 2003

(65) Prior Publication Data

US 2003/0176790 A1    Sep. 18, 2003

Related U.S. Application Data

(63) Continuation of application No. 09/750,816, filed on Dec. 28, 2000, now Pat. No. 6,540,679.

(51) Int. Cl.
*A61B 5/00* (2006.01)

(52) U.S. Cl. ............ 600/427; 600/439; 600/440; 600/549; 601/3

(58) Field of Classification Search ......... 600/407, 600/427, 424, 439, 440, 549; 601/2–4
See application file for complete search history.

(56) References Cited

U.S. PATENT DOCUMENTS

| | | | |
|---|---|---|---|
| 4,484,569 A * | 11/1984 | Driller et al. | 600/439 |
| 4,860,732 A | 8/1989 | Hasegawa et al. | |
| 4,896,673 A * | 1/1990 | Rose et al. | 600/439 |
| 5,224,467 A | 7/1993 | Oku | |
| 5,230,338 A | 7/1993 | Allen et al. | |
| 5,503,320 A | 4/1996 | Webster et al. | |
| 5,526,812 A | 6/1996 | Dumoulin et al. | |
| 5,577,991 A | 11/1996 | Akui et al. | |
| 5,609,562 A | 3/1997 | Kaali | |
| 5,617,858 A | 4/1997 | Taverna et al. | |
| 5,638,819 A | 6/1997 | Manwaring et al. | |
| 5,647,373 A | 7/1997 | Paltieli | |
| 5,685,820 A | 11/1997 | Riek et al. | |
| 5,701,900 A | 12/1997 | Shehada et al. | |
| 5,720,287 A | 2/1998 | Chapelon et al. | |
| 5,727,554 A | 3/1998 | Kalend et al. | |
| 5,748,767 A | 5/1998 | Raab | |
| 5,817,013 A | 10/1998 | Ginn et al. | |
| 5,891,034 A | 4/1999 | Bucholz | |
| 5,997,471 A | 12/1999 | Gumb et al. | |
| 6,004,262 A | 12/1999 | Putz et al. | |
| 6,050,943 A | 4/2000 | Slayton et al. | |

(Continued)

*Primary Examiner*—Ruth S. Smith
(74) *Attorney, Agent, or Firm*—Snell & Wilmer LLP

(57) ABSTRACT

A non-invasive visual imaging system is provided, wherein the imaging system procures an image of a transducer position during diagnostic or therapeutic treatment. In addition, the system suitably provides for the transducer to capture patient information, such as acoustic, temperature, or ultrasonic images. For example, an ultrasonic image captured by the transducer can be correlated, fused or otherwise combined with the corresponding positional transducer image, such that the corresponding images represent not only the location of the transducer with respect to the patient, but also the ultrasonic image of the region of interest being scanned. Further, a system is provided wherein the information relating to the transducer position on a single patient may be used to capture similar imaging planes on the same patient, or with subsequent patients. Moreover, the imaging information can be effectively utilized as a training tool for medical practitioners.

43 Claims, 10 Drawing Sheets

U.S. PATENT DOCUMENTS

| | | |
|---|---|---|
| 6,216,029 B1 | 4/2001 | Paltieli |
| 6,325,758 B1 | 12/2001 | Carol et al. |
| 6,361,531 B1 | 3/2002 | Hissong |
| 6,390,982 B1 | 5/2002 | Bova et al. |
| 6,540,679 B1 * | 4/2003 | Slayton et al. .............. 600/439 |
| 2002/0062077 A1 | 5/2002 | Emmenegger et al. |
| 2004/0102697 A1 * | 5/2004 | Evron ........................ 600/424 |

* cited by examiner

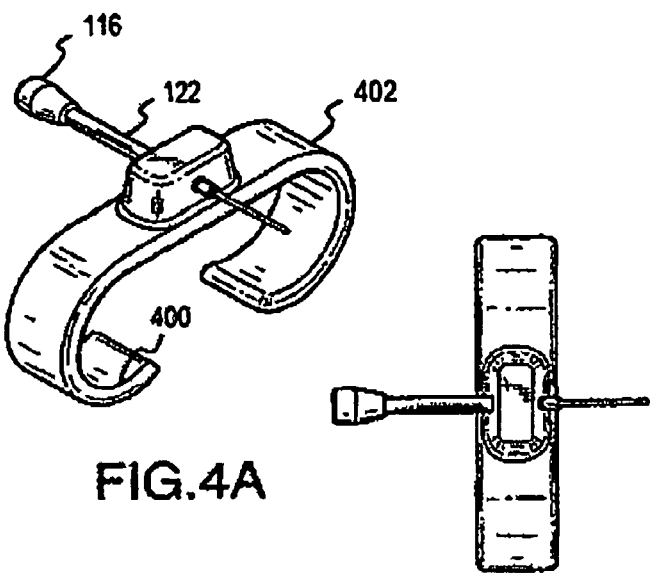
FIG.4A
FIG.4D
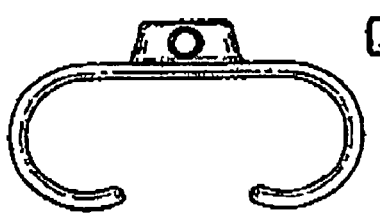
FIG.4B
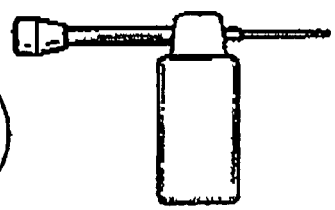
FIG.4E
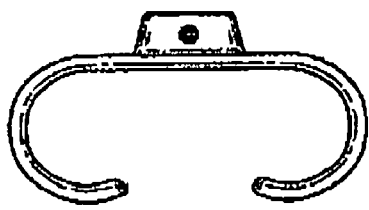
FIG.4C
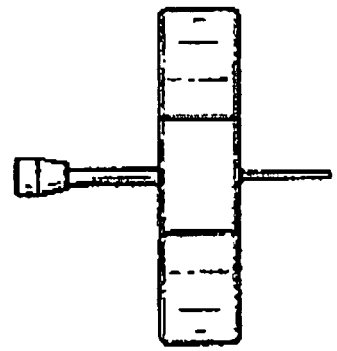
FIG.4F

VISUAL IMAGING SYSTEM FOR ULTRASONIC PROBE

This invention is a continuation of and claims priority to U.S. patent application Ser. No. 09/750,816, now U.S. Pat. No. 6,570,679, entitled "VISUAL IMAGING SYSTEM FOR ULTRASONIC PROBE," filed on Dec. 28, 2000, issued as U.S. Pat. No. 6,540,679 on Apr. 1, 2003, incorporated herein by reference.

BACKGROUND OF THE INVENTION

1. Field of the Invention

This invention generally relates to a non-invasive ultrasonic system, and more particularly, to a system which is capable of generating ultrasonic imaging data and information related to the positioning of a transducer during medical treatment and diagnosis.

2. Description of the Related Art

There are a number of well known non-invasive imaging techniques for the diagnosis and treatment of patients. These techniques generally allow a physician to obtain high fidelity views of the human anatomic structure without the advent of invasive procedures. Such imaging systems which provide a cross-sectional (tomographic) view of the human body include computer-aided tomography (CAT scans) x-ray imagers, magnetic resonance (MRI) imagers, positron emission tomographic scanning (PET), and magnetoencephotographic scanning (MEG). Typically, when a patient is scanned using one of these conventional cross-sectional imaging techniques, the patient's entire body or limb is imaged or mapped and the resulting anatomic topology is stored in an imaging database for later use.

While CAT scans, MRI's, PET's, and MEG's allow imaging of the entire body or entire limb requiring treatment, ultrasonic hand-held transducers are generally used to, obtain a more localized image of a treatment area. In general, the hand-held transducer contains an imaging element which includes an ultrasonic sensor for placing in contact with the patient's skin. During operation, the imaging element of the transducer sends ultrasonic waves from the transducer into the patient's body to the region of interest, and scattered waves reflected from the region of interest within the body are collected by an ultrasonic sensor within the transducer. The resulting electrical signals can then be processed to produce an image corresponding to the structure imaged by the transducer.

Many imaging systems, such as, those described above, include a feature that allows the operator to indicate the source or location of the scanned image. In particular, the operator makes use of a model pattern representing the human body. In marking the location of the recorded image, the operator places a specially configured cursor representing the image plane of the scanning device over a model pattern to illustrate the imaging plane's orientation with respect to the patient's body.

For hand-held transducers, however, any movement of the transducer's orientation with respect to the patient's body changes the orientation of the imaging plane. This change in the imaging plane thereby requires the operator to readjust the specially configured cursor with respect to the model pattern. As a consequence, if the patient's body shifts between taking images, or if the transducer must be repositioned after imaging, it is often difficult to recapture the prior image location.

Moreover, an additional problem associated with the aforementioned scanning techniques is that each imaging process is particular to a patient, and thus sensitive to the patient's position with respect to the imaging device. Therefore, each set of images has a discrete, unique orientation related to a single patient resulting from a single scanning session. Because of their unique or distinct features, images formed at different times, or from different vantage points, cannot be suitably compared on a point-by-point basis. This prevents an accurate comparison of the scanning regions from one scanning session to another, and from one patient to another. Such a comparison would be desirable in cases where the practitioner wishes to accurately compare scanned images from a healthy patient to the images of the patient undergoing the treatment, or where a practitioner wants to assess the responsiveness or improvements of a patient to a particular treatment. When such a comparison is desired, a system which enables the practitioner to place a transducer or other medical device in a prior imaging position would be tremendously beneficial.

Prior art systems for aiding or guiding the positioning of medical devices are generally cumbersome and complex. For example, U.S. Pat. No. 5,748,767 issued to Raab discloses a method for aiding a medical practitioner in the re-positioning of a surgical tool in a prior location, such as when the patient has moved. This re-positioning of the apparatus is accomplished by providing a correlation between the coordinates of the pre-treatment image and the image acquired during the treatment procedure. In addition, Raab necessarily requires the use of an apparatus which can transpose the imaging information from the reference system of the imaging system to the reference system of the apparatus. The system disclosed in Raab provides a method to enable the surgical tool to be positioned and re-positioned in relatively the same position with an acceptable accuracy by coordinating the pre-treatment and treatment reference systems.

During operation of the Raab system, the pre-treatment and treatment coordinates are continually calculated with respect to a specially designed reference block attached to an electrogoniometer. The electrogoniometer is further used to determine the orientation of the instruments used in the treatment process. This system, however, uses a mechanical linkage for maintaining the surgical tool in a fixed relationship with the reference block. Such machinations of the probing process creates a system that is relatively cumbersome for the practitioner using a hand-held transducer.

An additional problem with existing systems is found in the difficulty with which a prior imaging plane can be recaptured for comparison purposes, a problem which becomes even more significant with the use of hand-held transducer. For example, in one therapeutic application using a hand-held transducer, the objective of the treatment is to create a very well-placed thermal gradient in the treatment area to selectively destroy certain regions thereof. An example of this is the hypothermia technique wherein a temperature near about 43 degrees Celsius is required to be maintained in the specific treatment area, or the focused ultrasound surgery technique which has a goal of elevating the treatment area temperature to above and beyond 55 degrees Celsius. During the therapeutic treatment process, the physiological response of the target tissue is directly related to the spatial extent and temporal duration of the heating pattern. Consequently, in order to appropriately perform feedback and control of the therapeutic treatment process, it is absolutely essential to control the temperature in the target tissue so as to know whether or not the temperature in the treatment region has been raised to a level that produces a desired therapeutic effect or the destruction of the tissue. Moreover, as with the hypothermia and focused ultrasound surgery techniques, and any other technique whereby the success of the therapy must be evaluated from one treatment session to the next, it is critical to be able to accurately image the treatment area undergoing treatment for comparison to subsequent treatment sessions.

Another method for enabling a particular image to be recaptured from one session to the next may be accomplished by using a three-dimensional coordinate system that is fixed within a human anatomy. For example, U.S. Pat. No. 5,230,338 issued to Allen et al. discloses a method for interactively guiding a surgical tool, wherein three or more fiducial implants are implanted in three separate, spaced locations within the human body. With the Allen method, the three fiducial implants are arranged in a non-collinear manner such that a plane is formed which defines a three dimensional coordinate system. Once the external coordinate system is established, a scan of the treatment area is performed. During subsequent scans, the patient's orientation may change relative to the imaging apparatus, but the new orientation of the patient can be measured by locating the fiducial implants in relation to the imaging apparatus. In this manner, the images of subsequent scans of a patient relating to a new position or orientation can be configured to correspond to the earlier recorded scans for comparison. A disadvantage inherent in the Allen system, however, is that the fiducial implants remain implanted in the patient between imaging session. In addition, the Allen system does not facilitate the scanning or diagnosis of other patients, but only operates effectively for the same patient.

As described above, several prior art techniques exist for monitoring and recording the position of tools used in the diagnosis and treatment of patients, or for recapturing an image scanned in a prior scanning session. Generally, these techniques are complex as in the U.S. Pat. No. 5,748,767 issued to Raab, or are limited in their use, as in U.S. Pat. No. 5,230,338 issued to Allen et al. That is, use of such techniques essentially requires the implementation of cumbersome equipment, such as an electrogoniometer and reference block, or requires that elements of the system remain with the patient between scans, such as the implants in Allen. In that regard, such methods are inadequate for medical specialist who desire a simpler and less cumbersome manner to record a tool position or orientation which correlates with a prior image, to facilitate the return to the precise location of the prior treatment in that patient or, alternatively, a second patient undergoing similar treatment.

Thus, a need exists for a less cumbersome and easy to use system capable of monitoring and recording the position of a transducer to facilitate the desired-positioning of the transducer within a treatment area.

SUMMARY OF THE INVENTION

A visual imaging system in accordance with the present invention overcomes various problems of the prior art. In accordance with various aspects of the present invention, a noninvasive visual imaging system is provided, wherein the imaging system procures an image of a transducer position during diagnostic or therapeutic treatment. In addition, the system suitably provides for the transducer to capture patient information, such as acoustic, temperature, or ultrasonic images. For example, an ultrasonic image captured by the transducer can be correlated or otherwise fused or combined with the corresponding positional transducer image, such that the corresponding images represent not only the location of the transducer with respect to the patient, but also the ultrasonic image of the region of interest being scanned.

In accordance with another aspect of the present invention, the imaging system can comprise a positioning indicator located within the transducer which can facilitate the determination of the position and/or orientation of the transducer with respect to the patient. In addition, this positioning information can be utilized to suitably scale the ultrasonic image of the treatment region to correspond with the positional image of the patient to provide a fused image.

Further, in accordance with another aspect of the present invention, a system is provided wherein the information relating to the transducer position on a single patient may be used to capture similar imaging planes on the same patient, or with subsequent patients. This information captured may also be utilized for training purposes.

BRIEF DESCRIPTION OF THE DRAWINGS FIGURES

A more complete understanding of the present invention may be derived by referring to the various exemplary embodiments of the present invention which are described in conjunction with the appended drawing figures in which like numerals denote like elements, and in which:

FIGS. 4A–4F illustrate an exemplary embodiment of an attachment device in accordance with the present invention;

DETAILED DESCRIPTION OF VARIOUS EXEMPLARY EMBODIMENTS

Figure 1:
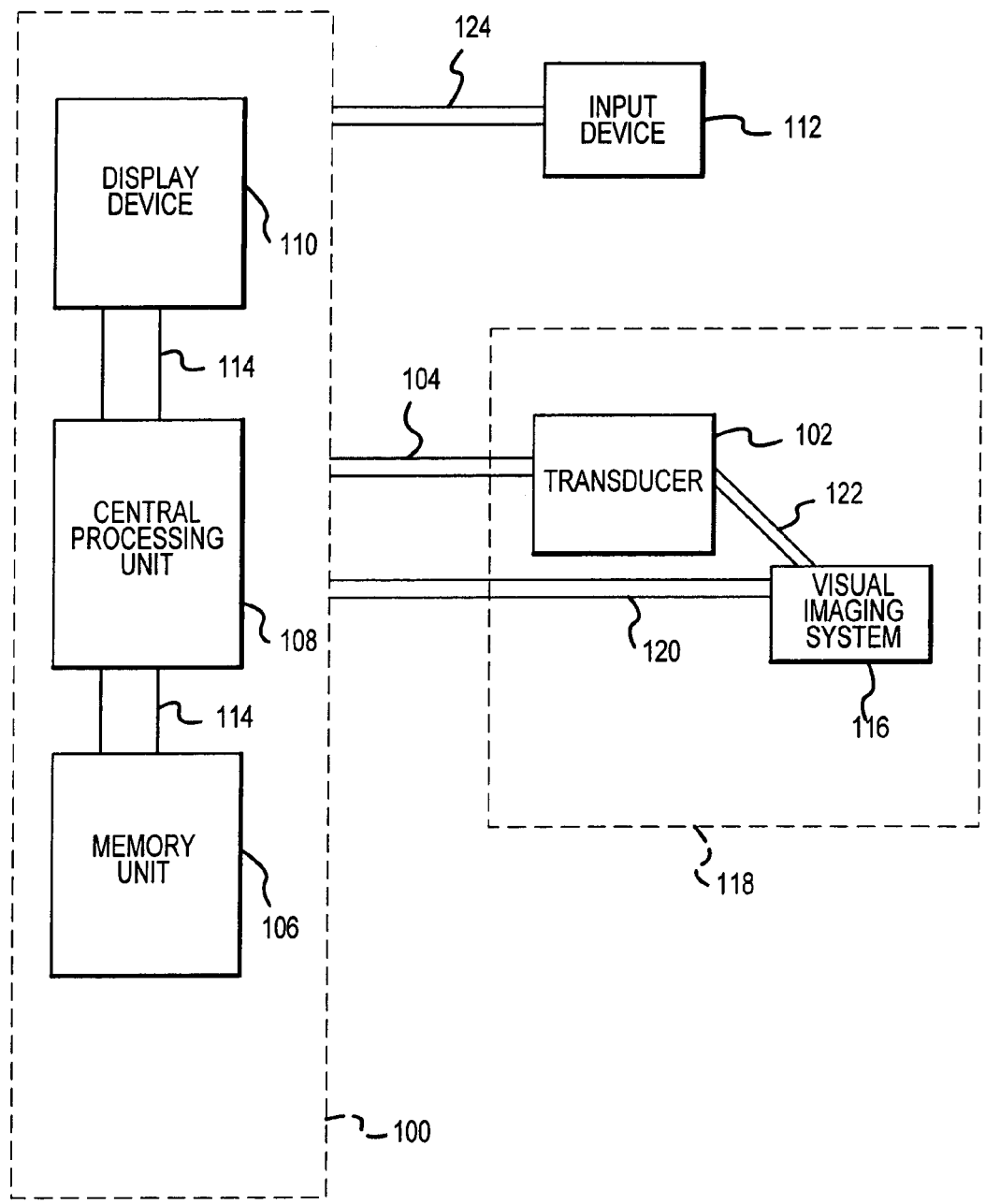
FIG. 1 illustrates a block diagram of an exemplary embodiment in accordance with the present invention.

The present invention may be described herein in terms of various components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, those skilled in the art will appreciate that the present invention may be practiced in any number of medical contexts and that the exemplary embodiment relating to an ultrasonic transducer as described herein is merely one exemplary application for the invention. For example, the principles, features and methods discussed may be applied to any medical application. Further, various aspects of the present invention may be suitably applied to other industrial, manufacturing or engineering applications, such as the inspection of materials such as steel, plastics, concrete or wood.

In accordance with one aspect of the present invention, a medical treatment and diagnosis system comprises a visual imaging system suitably configured with a probe assembly to facilitate the accurate and consistent placement of the probe assembly during treatment and diagnosis of a patient. The probe system can be suitably configured to perform any of various functions, such as the obtaining of information relating to a region of interest of the patient, and/or the providing of therapeutic treatment of the region of interest. In addition, the probe system can comprise various medical devices, such as transducers for imaging, heating or temperature measurement, audio devices, or any other device for obtaining patient information.

The visual imaging system is suitably configured to provide information relating to the position of the probe system with respect to the patient, or the region of interest. This information can include various forms, such as, for example, video or photographic images, or graphical representations, relating to the position of the probe system during operation. Moreover, the visual imaging system can comprise various components, such as video or other like imaging devices. In addition, the visual imaging can be configured directly within, or connected to, the probe system to facilitate the identification of the positional information of the probe system during its use.

In accordance with another aspect of the present invention, the visual imaging system is suitably configured to provide information relating to the position of the probe system to a control system for further assessment and recommendations. In accordance with this aspect, the control system is configured to receive imaging information from the visual imaging system and patient information from the probe system and suitably correlate both components of information to provide various advantages to the medical practitioner. For example, the control system can provide information which facilitates the positioning of the probe system during use. This information could be a reference position of the probe system from a prior use of the probe with a particular patient, or from other patients. In addition, the control system could provide information directing the probe system to a specific position of the patient to observe or treat a particular region of interest for that patient. Further, this imaging information can be suitably utilized for the training of medical practitioners.

To further explain in more detail various aspects of the present invention, exemplary embodiments of a visual imaging system as used with a control system and an ultrasonic probe system will be provided. However, it should be noted that the following exemplary embodiments are for illustrative purposes, and that the present invention can comprise various other configurations for a medical treatment and diagnostic system. In addition, although not illustrated in the drawing figures, the medical treatment and diagnostic system can further include components associated with a therapy or diagnostic system, such as any required power sources, system control electronics or additional memory locations.

With reference to FIG. 1, an exemplary embodiment of a medical treatment and diagnostic system in accordance with the present invention is shown. In accordance with this embodiment, the system comprises a probe assembly 118 and a control system 100. Probe assembly 118 suitably comprises a transducer 102 for rendering localized diagnosis and treatment of patients and a visual imaging system 116 for transmitting information to control system 100 relating to the position and/or orientation of transducer 102 with respect to the patient. Transducer 102 may comprise any conventional type of transducer used by practitioners in the diagnosis or treatment of patients. Preferably, transducer 102 comprises an ultrasonic transducer configured to provide various features. For example, transducer 102 can include a visual imaging element capable of imaging a patient's treatment region. Transducer 102 can also be configured for recording or measuring acoustic or temperature data and for transmitting the acoustic or temperature data to the control unit 100 via communications channel 104. Further, transducer 102 can be suitably configured to providing therapeutic treatment to the region of interest. In accordance with an exemplary embodiment, transducer 102 can comprise a U.S. Pat. No. 6,050,943, entitled IMAGING, THERAPY AND TEMPERATURE MONITORING ULTRASONIC SYSTEM and issued on Apr. 18, 2000, as well as a three-dimensional ultrasonic image as disclosed more fully in U.S. patent application Ser. No. 09/502,174, now U.S. Pat. No. 6,500,121, entitled IMAGING, THERAPY AND TEMPERATURE MONITORING ULTRASONIC SYSTEM, both hereby incorporated herein by reference.

Visual imaging system 116 may comprise any conventional device capable of capturing visual information relating to the position and/or orientation of transducer 102 and for transmitting the information to control device 100, via such as signal cable 120. For example, imaging system 116 can comprise a video camera for capturing real-time or substantially-realtime visual information. Visual imaging system 116 can also comprise a photographic camera for providing still-photos representative of the position and/or orientation of transducer 102.

In addition, visual imaging system 116 can be suitably connected to transducer 102 to follow the movement of transducer 102 during operation. As a result, a transducer 102 moves about the patient, visual imaging system 116 can suitably follow along in real-time. This connection can be facilitated by various devices and in various manners. In addition, visual imaging system 116 can be permanently or removeably attached to transducer 102. Further, the position and/or orientation of visual imaging system 116 with respect to transducer 102 can be suitably configured in various manners, as will be described in more detail below. As a result, the positional and/or orientation information of transducer 102 can be correlated with any imaging, acoustic or temperature measurements obtained by transducer 102.

Control system 100 is configured to control the operation of probe assembly 118, including the receiving of information from probe assembly, such as from transducer 102 and imaging system 116. In addition, control system 100 can be configured to process the information collected from transducer 102 and imaging system 116. From this processed information, control system 100 can provide various types of information to the medical practitioner.

For example, control system 100 can indicate to the practitioner a desired position and/or orientation of transducer 102 based on the prior use of probe assembly 118 with the present patient being observed. In addition, control system 100 can also provide information based on use of probe assembly 118 for other patients. Moreover, control system 100 can include a historical database of previous applications of probe assembly 118. This database can provide position and/or orientation information for a particular region of interest, and can be utilized for further review and diagnosis of the patient, as well as being used for training of medical practitioners.

Control system 100 can comprise various hardware configurations. In accordance with an exemplary embodiment, control system 100 comprises a memory unit 106, a central processing unit 108, and a display device 110. The memory unit 106 of control system 100 may be of any conventional type capable of storing a plurality of data and software programs, including video, audio, numerical or statistical data. Memory unit 106 is suitably configured to provide memory locations for storing various items of data to be directly or indirectly input to, or directly or indirectly output from, control system 100. Memory unit 106 can also comprise a conventional database for the storage of a plurality of data and software programs, including video, audio, numerical or statistical data. For example, video streaming of the positional imaging information and ultrasonic imaging information of transducer 102 during operation may be suitably stored, such as a segment of a couple seconds, minutes or longer, or even still segments of information.

Memory unit 106 can be connected to central processing unit 108 in any conventional manner, such as, for example, through a bus 114. Central processing unit 108 is configured for receiving and decoding incoming instructions, executing commands, and manipulating data stored in memory unit 106. Central processing unit 108 may also be configured to receive instructions from an input device 112, such as any conventional type keyboard, for example, a touch-type or touch entry keyboard. The instructions from the input device 112 may further require the central processing unit 108 to retrieve data or software programs stored in memory unit 106. Central processing unit 108 is further capable of executing computer software programs and sending the processed information to display device 110.

Central processing unit 108 may comprise various software algorithms configured for correlating, fusing or otherwise combining acoustic, thermal, or ultrasonic imaging information from transducer 102 with the positional and/or orientation information from imaging device 116. For example, in accordance with an exemplary embodiment, and with momentary reference to FIGS. 7–10, the software algorithms can be configured to provide a combined image wherein the positional image of transducer 102 can be suitably displayed with the ultrasonic image of the patient to provide a "fused" image. In addition, such a fused or combined image can be suitably scaled to as to appear to provide a cross-sectional view of the patient and treatment region during operation of transducer 102.

Figure 2:
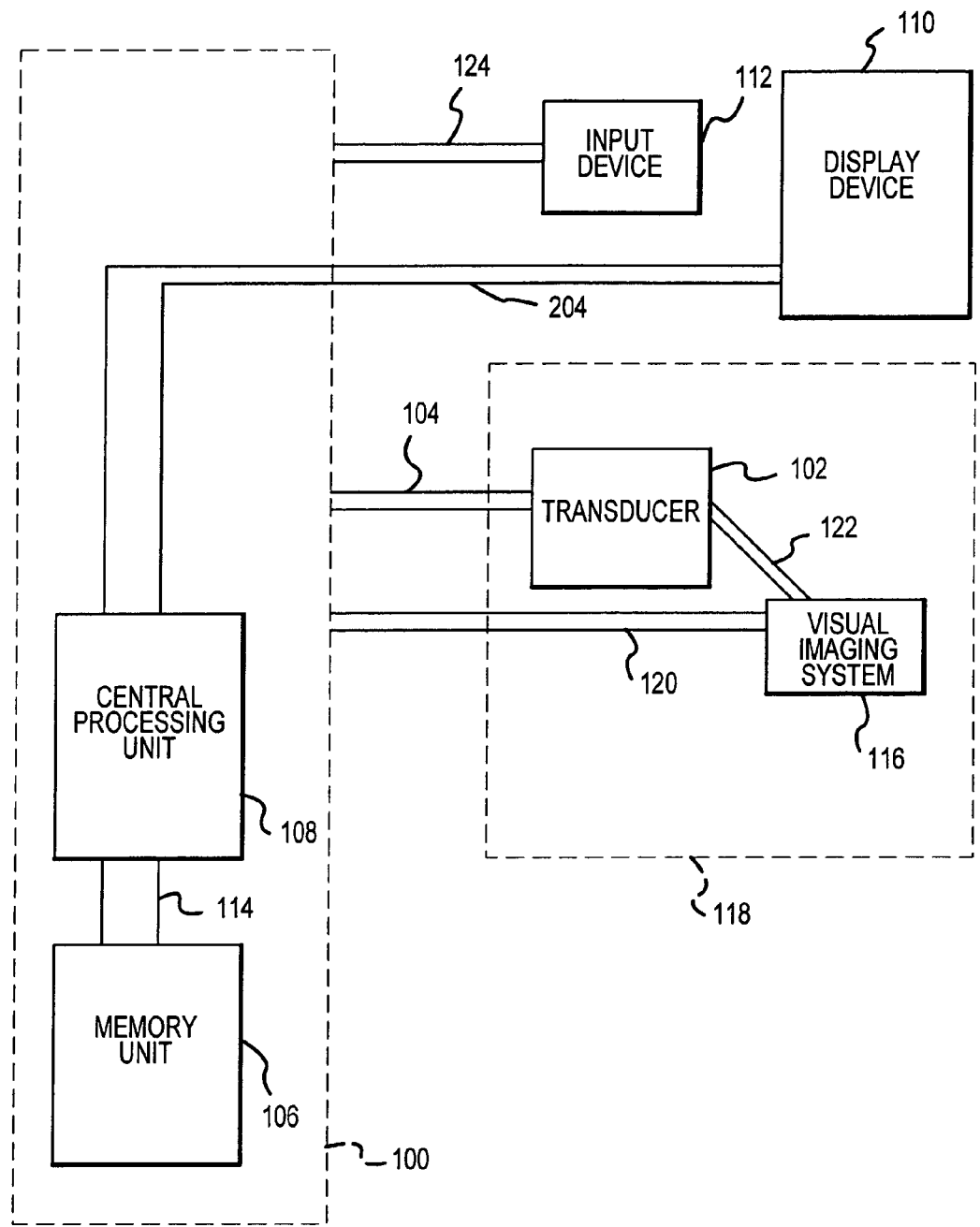
FIG. 2 illustrates a block diagram of another exemplary embodiment in accordance with the present invention.

Display device 110 suitably comprises any display for providing at least one of video, audio, graphical data or images. Display device 110 may be a component of control system 100, or display device 110 may be a separate device from control system 100, for example as is depicted in FIG. 2. Where display device 110 is apart from control system 100 as in FIG. 2, display device 110 can be connected to the control system 100 via communications channel 204. Further, display device 110 may also be of any conventional type capable of displaying data input through input device 112, stored in memory unit 106, or processed through processing unit 108. For example, display device 110 is capable of displaying video and ultrasonic images in simultaneous or singular fashion, for example, a fused image or separate images of the position of transducer 102 and the ultrasonic image of the patient.

Figure 3:
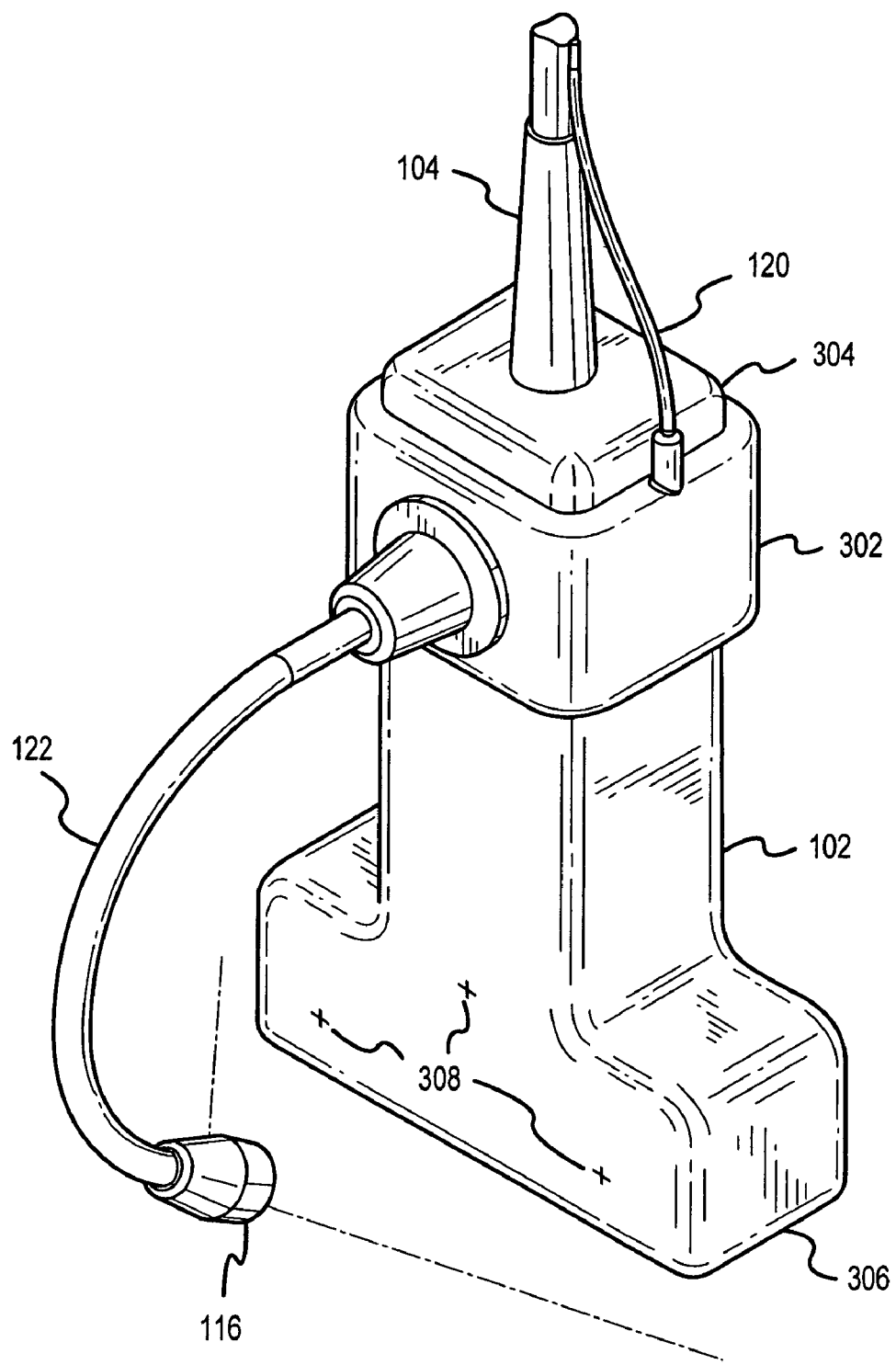
FIG. 3 illustrates an exemplary embodiment of a probe assembly in accordance with the present invention.

Referring now to FIG. 3, an exemplary embodiment of probe assembly 118 is illustrated. In accordance with this embodiment, transducer 102 further includes a transducer imaging element 306 encased within a transducer housing 304. Transducer imaging element suitably comprises a ultrasonic transducer element configured for sending ultrasonic signals to a region of interest and then suitably receiving signals to provide an ultrasonic image of the region of interest.

Visual imaging device 116, such as a video camera, can be suitably attached or connected to transducer 102 by various manners. For example, to connect imaging device 116 and transducer 102, an arm member 122 can be provided. Arm member 122 may be any configuration of attachment structure, and may comprise various materials, for example, plastics, metals or other like materials. In accordance with one embodiment, arm member 122 is adjustable. In this embodiment, arm member 122 can be suitably configured for moving with relative freedom to enable imaging device 116 to be suitably stationed in various positions with respect to transducer 102, i.e., the arm member can position imaging device 116 in various fixed positions with respect to transducer 102 to provide multiple views of transducer 102 with respect to the patient. For example, arm member can comprise a section of flexible conduit, such as that utilized in various adjustable lighting systems. Thus, arm member 122 can be suitably positioned, and/or re-positioned as desired by the medical practitioner. However, arm member 122 can also comprise a rigid or substantially rigid member configured to maintain a more permanent position of imaging device 116 relative to transducer 102. Accordingly, arm member 122 suitably facilitates the procurement of images relating to the position of the transducer 102 from imaging device 116 by providing a fixed position of imaging device 116 with respect to transducer 102 during operation.

Arm member 122, and thus visual imaging system 116 can be suitably attached or connected to transducer 102 in various manners. For example, transducer 102 can suitably include an attachment device 302. Attachment device 302 can be permanently or removeably affixed to transducer 102 such that when affixed, attachment device 302 is in continuous contact with the transducer housing 304 In addition, attachment device 302 can provide for the fixed connection of arm member 122 to transducer 102. Attachment device 302 can also comprise any material, for example, plastics, metals, wood and the like, and any configuration, for example, clamps, clips, clasps and the like, for facilitating connection or attachment of arm member 122 to transducer 102.

With momentary reference to FIGS. 4A through 4F, various perspective, top, bottom and side views of an exemplary attachment device 302 are illustrated. In this embodiment, the attachment device 302 comprises a clip 402. As shown, clip 402 is suitably designed as to be capable of being securely attached to transducer housing 304. In addition, the inner contour 400 of clip 402 is preferably shaped to the outer contour of transducer housing 304 such that once clip 402 is firmly attached to transducer housing 304, the position of clip 402, relative to transducer housing 304, is substantially fixed. As a result of attachment device 302 and arm member 122, the visual image transmitted by imaging device 116 can follow in a direct correlation to the movement and position of transducer 102.

Although FIG. 4 depicts a clip 402 wherein the clip is formed to fit securely and immobile to a transducer housing, it should be noted that clip 402 is not so limited. That is, imaging device 116 and arm member 122 may be affixed to the transducer housing 304 using any conventional mechanism which ensures that once arm member 122 is held substantially rigid or fixed, then the spatial relationship between imaging device 116 and transducer 102 remains substantially fixed. Accordingly, attachment device 302 may comprise any assembly or arrangement such that the attached components are rendered relatively fixed with respect to one another.

Figure 5:
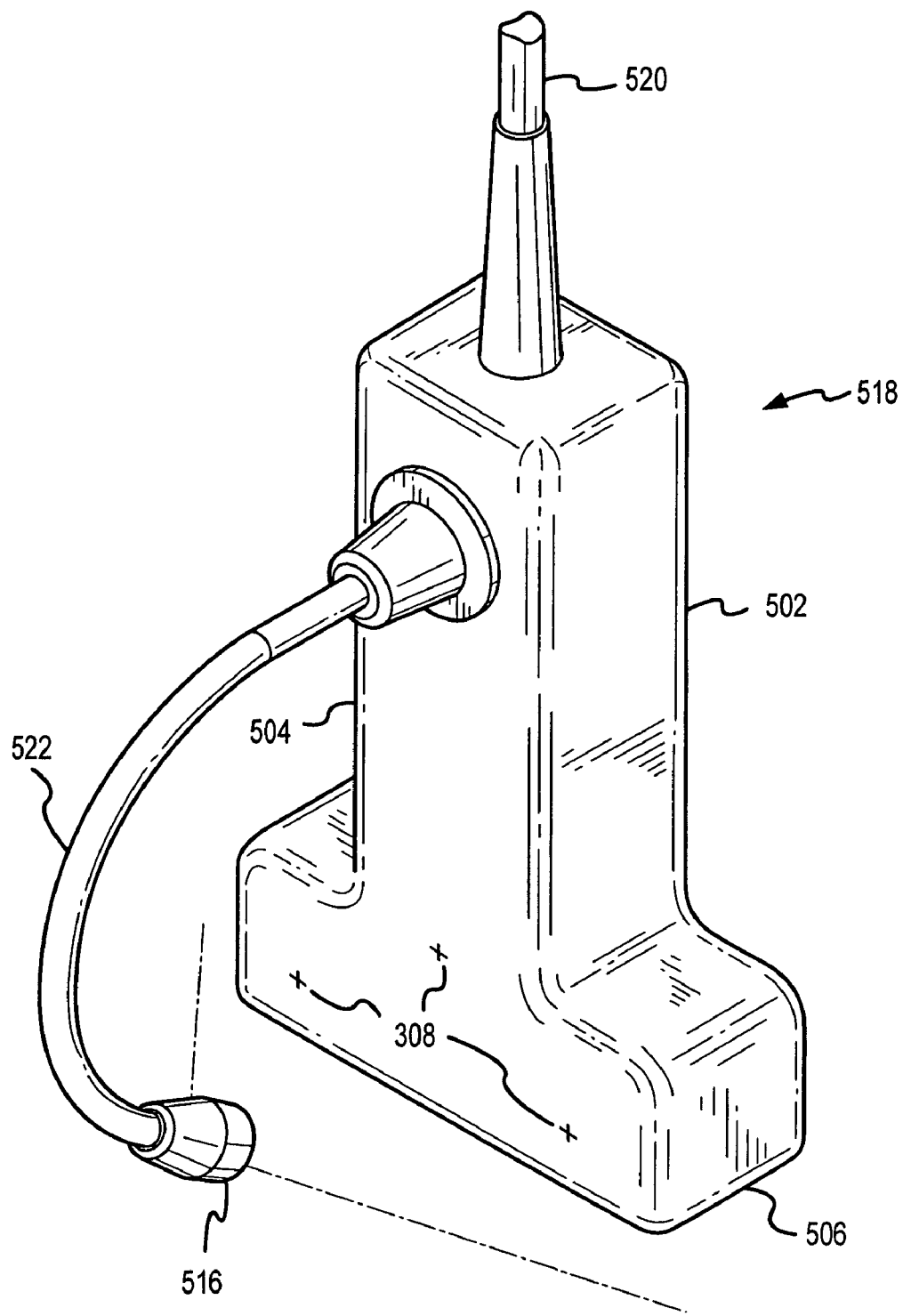
FIG. 5 illustrates another exemplary embodiment of a probe assembly in accordance with the present invention.

Although an attachment device 302 can facilitate attachment of arm member 122 to transducer 102, other methods and devices for connecting the components together can be utilized. For example, arm member 122 and transducer 304 can be suitably configured for integration of arm member 122 directly into transducer 102. With reference to FIG. 5, another exemplary embodiment of probe assembly 118 is illustrated. In accordance with this embodiment, a transducer 502, including a transducer housing 504 and transducer imaging element 506 are provided. In addition, an arm member 522 is suitably integrated into transducer housing 504. Further, this exemplary embodiment of the probe assembly 118 includes imaging device 516 attached to transducer 502 via arm member 522. It should be noted that transducer 502, imaging device 516 and arm member 522 are similar in characteristics and operation to transducer 102, visual imaging device 116 and arm member 122 described above. In addition, probe assembly 118 includes a transducer cable 520 which is capable of transmitting data from transducer sensor 506 and visual images from imaging device 516 to control unit 100.

In accordance with another aspect of the present invention, probe assembly 108 may be configured to provide a fused image for display which is representative of the combining of the position and/or orientation information of transducer 102 and the ultrasonic imaging information of the treatment region. This fusing of images can be suitably provided by software algorithms within control system 100. While this fusing of images can be readily provided once the orientation and position of transducer 102 is known, once transducer 102 is moved or tilted such that the angle of scan or the geometry of transducer 102 with respect to the patient changes, the scaling of the ultrasonic imaging information needs to be reconfigured.

To further facilitate the providing of a fused image which represents an image similar to a cross-sectional view of transducer 102 and patient, for example, as illustrated in FIGS. 7–10, transducer 102 can be configured with a positioning indicator. With reference to FIG. 3, an exemplary positioning indicator 308 is illustrated.

In accordance with this exemplary embodiment, positioning indicator 308 comprises a series of marks which are suitably configured to facilitate the determination and assessment of the positional and/or orientation information of transducer 102 with respect to the patient. Positioning indicator 308 is suitably configured to permit control system 100 to suitably correlate the geometry, i.e., position and orientation, of transducer 102 to the geometry of a corresponding ultrasonic image of the treatment region. For example, positioning indicator 308 can comprise triangulation marks, i.e., three marks configured in a triangular manner, configured at known distances apart to permit the software algorithm of central processing unit 108 to assess and determine the orientation and geometry of transducer 102 during operation.

Figure 10:
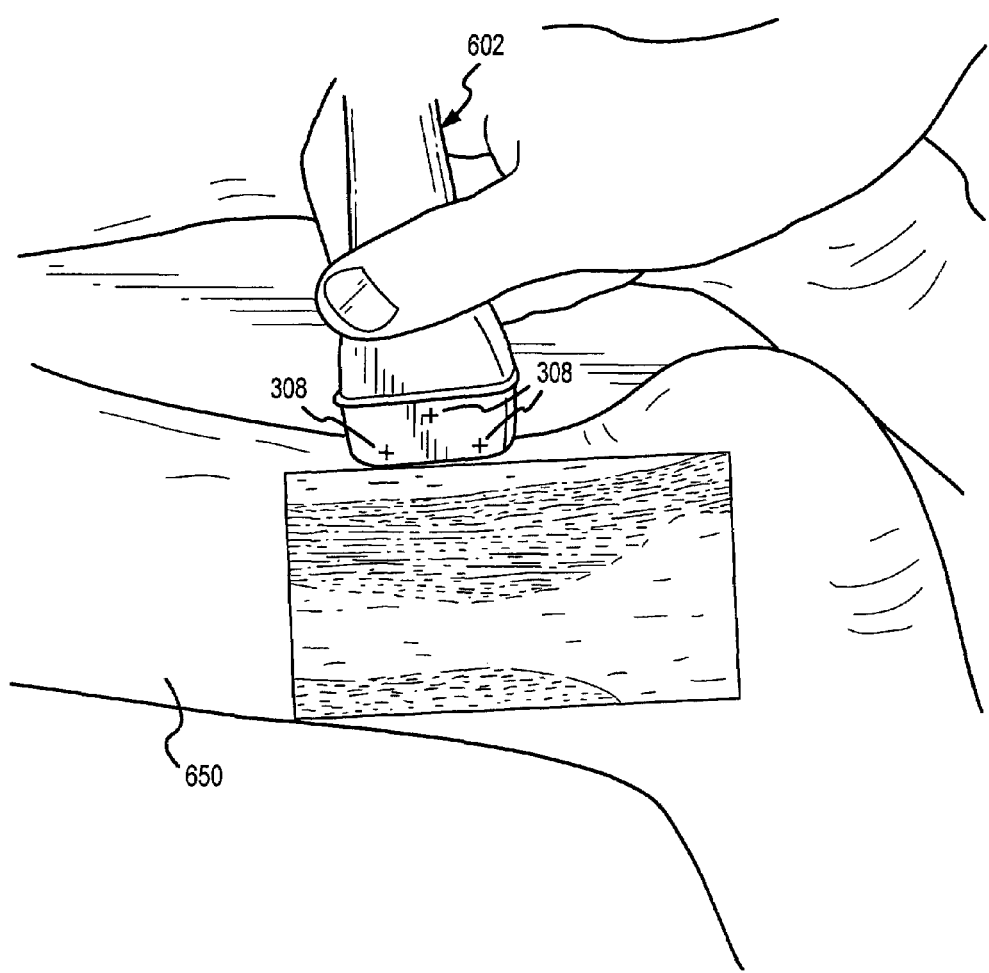
FIG. 10 illustrates an exemplary embodiment of the visual imaging system in operation as may be displayed in accordance with the present invention.

For example, transducer 102 can include three cross-like triangulation marks, 1 mm in length, separated by fixed distances, e.g., 3 to 10 mm or more apart, that can provide the software with a reference point for the orientation of transducer 102. In addition, by knowing the fixed distances of the triangulation marks, the software within central processing unit 108 can determine the position and distance of imaging device 116 with respect to transducer 102. Thus, as transducer 102 changes the angle of scan or otherwise the orientation with respect to the region of interest, the software within central processing unit 108 can suitably follow these changes in orientation and position. Accordingly, by knowing the orientation and geometry of transducer 102 with respect to the patient, positional and/or orientation information and ultrasonic imaging information can be suitably fused into a combined image. In addition, the respective positional and/or orientation information and ultrasonic imaging information can be suitably scaled by the software algorithm to provide an image similar to a cross-sectional view of transducer and treatment region, such as is illustrated in FIG. 10.

While an exemplary embodiment of a positioning indicator can comprise a series of marks 308, such as two, three, four or more, or a single mark, positioning indicator 308 can comprise any mechanism for facilitating the determination of the geometry of transducer 102 with respect to the patient. Thus, the positioning indicator can also comprise any three-dimensional positioning indicator devices that can provide information regarding the position of transducer 102 with respect to the patient. For example, the positioning indicator can comprise an electromagnetic device configured within transducer 102 that can be suitably tracked by electromagnetic sensors configured with control system 100. In addition, the positioning indicator can comprise a gravitational accelerometer configured to provide the assessment of three axis or rotation of transducer 102 in three dimensions. Such a collection of three-dimensional information could also be suitably correlated with three-dimensional imaging information, as disclosed more fully in U.S. patent application Ser. No. 09/502,174, now U.S. Pat. No. 6,500,121, entitled IMAGING, THERAPY AND TEMPERATURE MONITORING ULTRASONIC SYSTEM, hereby incorporated herein by reference.

Having described various aspects and features of a probe assembly and control system, the operation of an exemplary embodiment of the present invention will now be described. With respect to the following description, the operation of ultrasonic transducers will not be described in great detail. Although the present embodiment will be described with respect to the use of an ultrasonic transducer, it is to be understood that the present invention is not so limited. For example, the present invention may be used with any extra-corporeal probe or transducer used in the diagnosis or treatment of patients, such as general radiology, OB/GYN, breast, musculoskeletal, and other imaging or treatment applications.

Figure 6:
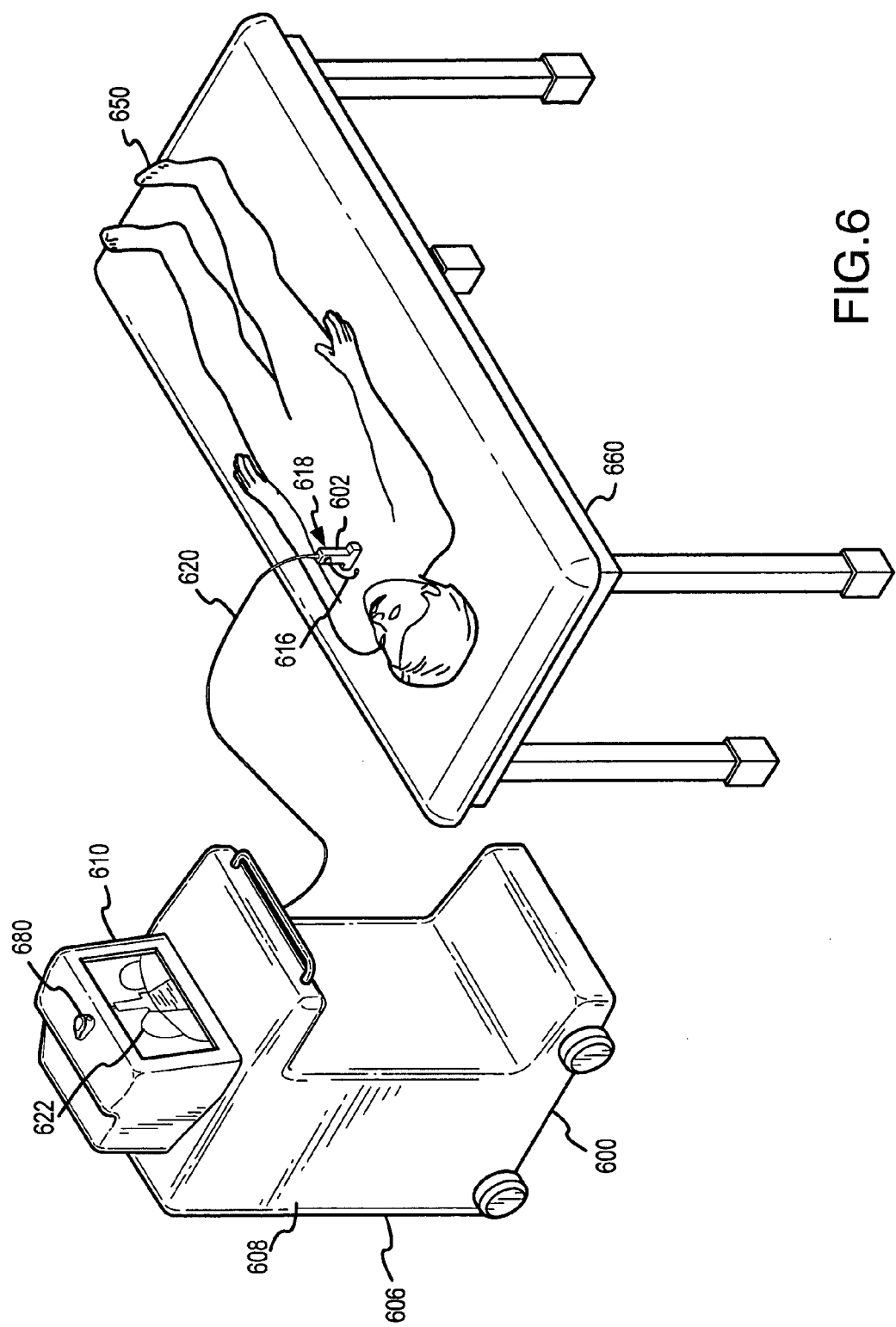
FIG. 6 illustrates an exemplary embodiment of the visual imaging system in operation in accordance with the present invention.

With reference to FIG. 6, an exemplary embodiment of the present invention during operation is illustrated. In accordance with this embodiment, a patient 650 is illustrated lying on a treatment table 660 while undergoing treatment or diagnosis in accordance with the present invention. The medical treatment and diagnosis system includes a control system 600 and a display device 610, wherein both the control system 600 and the display unit 610 comprise characteristics to the like elements of FIGS. 1 and 2. Further, a probe assembly 618 is included for providing imaging and treatment features, such as the probe assembly described in more detail above.

During operation, the medical practitioner, not shown, can manually image a treatment area of patient 650 by scanning the patient with probe assembly 618. Transducer 602 of probe assembly 618 images the treatment area and sends an ultrasonic image to the control system 600 via data cable 620. Meanwhile, visual imaging device 616, such as a video camera, of probe assembly 618 captures a visual image of the position and/or orientation of transducer 602 with respect to the patient treatment area, and transmits the visual image to the control system 600, also via data cable 620. The treatment area comprises the region of interest that the practitioner has determined the scanning will occur using the transducer 602.

Once the control system 600 receives the visual position and/or orientation images from imaging device 616 and the transducer image from transducer 602, the processing unit 608 suitably processes the images for further display and use. In addition, the images can be suitably transmitted to memory unit 606 for storage and later reference, for example, for training purposes or for use later with the same patient or other patients. During processing of the images by processing unit 608, the visual and transducer images can be suitably correlated into a combined image such that the resulting combined image comprises both the ultrasonic, acoustic and/or thermal treatment image information captured by the transducer 602 during operation and the positional image depicting the position and/or orientation of the transducer 602 on the surface of the treatment area at the time the transducer image is captured. Once the visual and transducer images are processed by central processing unit 608, such as by a suitable algorithm, the respective visual and transducer images, and/or the combined image, i.e., the fused image, can be sent to memory unit 606 for storage and later reference. In addition, the respective images and/or the combined image can be further transmitted to the display device 610 for interpretation by the medical practitioner.

In accordance with another exemplary embodiment, the medical treatment and diagnosis system can include other visual imaging devices for capturing information regarding the position and/or orientation of the patient and the transducer. For example, other imaging devices or cameras can be located with the system, such as a probe assembly having two or more arm members suitably connected to two or more visual imaging devices. This configuration could provide different views of the position and/or orientation of the transducer, or even a three-dimensional view if desired. In addition, additional imaging devices could be included from within or proximate the control system or display, such as an additional visual imaging device 680. Moreover, other systems for determining the position of a medical instrument, such as the triangulation methods described above, can be combined with the probe assembly of the present invention.

The positional and/or orientation image and the transducer image can be configured in various manners. For example, display 610 can be configured to display each image separately, for example, on an individual screen basis, or on the same screen, such as a split screen or a "picture-in-picture" concept as is utilized on various television or computer monitors. In addition, in accordance with an exemplary embodiment, the images can be configured in a combined image which facilitates the analysis and assessment of the image information during or after operation.

Figure 7:
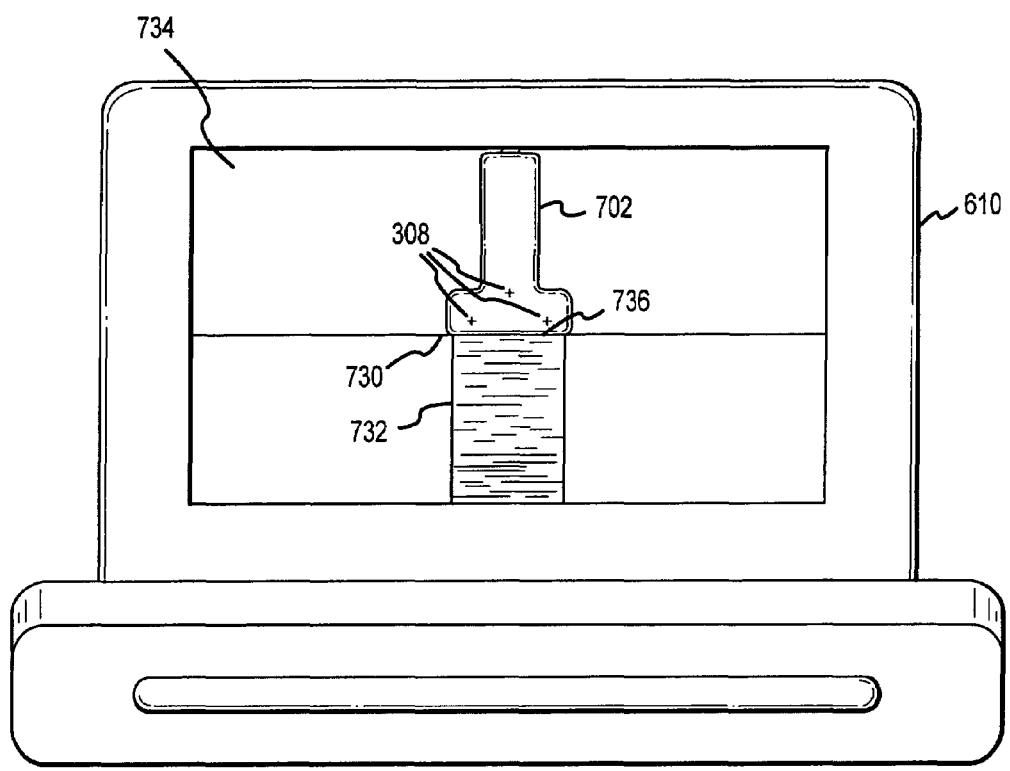
FIG. 7 illustrates an exemplary combined image capable of being shown on the display screen in accordance with the present invention.

With reference to FIG. 7, and with continued reference to FIG. 6, a combined image in accordance with an exemplary embodiment is illustrated. In this embodiment, display device 610 suitably displays a combined image comprising a positional image 734, representative of the position and/or orientation of transducer 602, and a transducer image 732, such as the ultrasonic images of the treatment region received and processed by the central processing unit 608. In addition, the respective images can be suitably combined into a single image. For example, the single image can include positional image 734 with an inlay of transducer image 732, i.e., positional image 734 and transducer image 732 are suitably fused into a combined image which is representative of transducer 602 while in contact with the treatment area 736. In other words, the combined image can show the region of interest that is imaged under the patient's skin as represented by the transducer image 732, in correlation with the position and/or orientation of transducer 602 in contact with the patient's skin, as represented by positional image 734. As a result, a medical practitioner can view the combined image as if a cross-sectional view of the treatment region is available for assessment, i.e., the combined image is similar to a cross-sectional view of the patient and the treatment region. For example, with reference to FIG. 10, as transducer 602 is obtaining an ultrasonic image of a patient's heel, leg or foot 650, a combined image displaying the position and orientation of transducer fused together with a suitably scaled ultrasonic image of patent 650 is provided. Moreover, as transducer 602 is moved about the patient, the combined image can be suitably scaled on a real-time basis by software algorithms within control system 600, such as described above. As will be discussed below, such a combined image provides various advantages.

Figure 8:
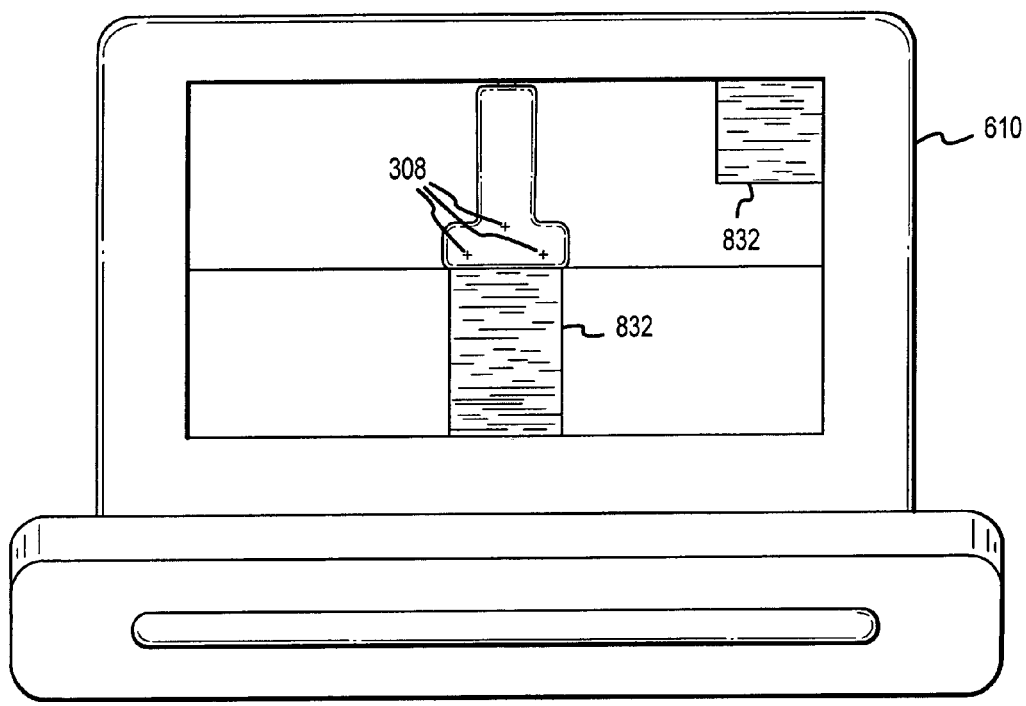
FIG. 8 illustrates another exemplary combined image capable of being shown on the display screen in accordance with the present invention.
Figure 9:
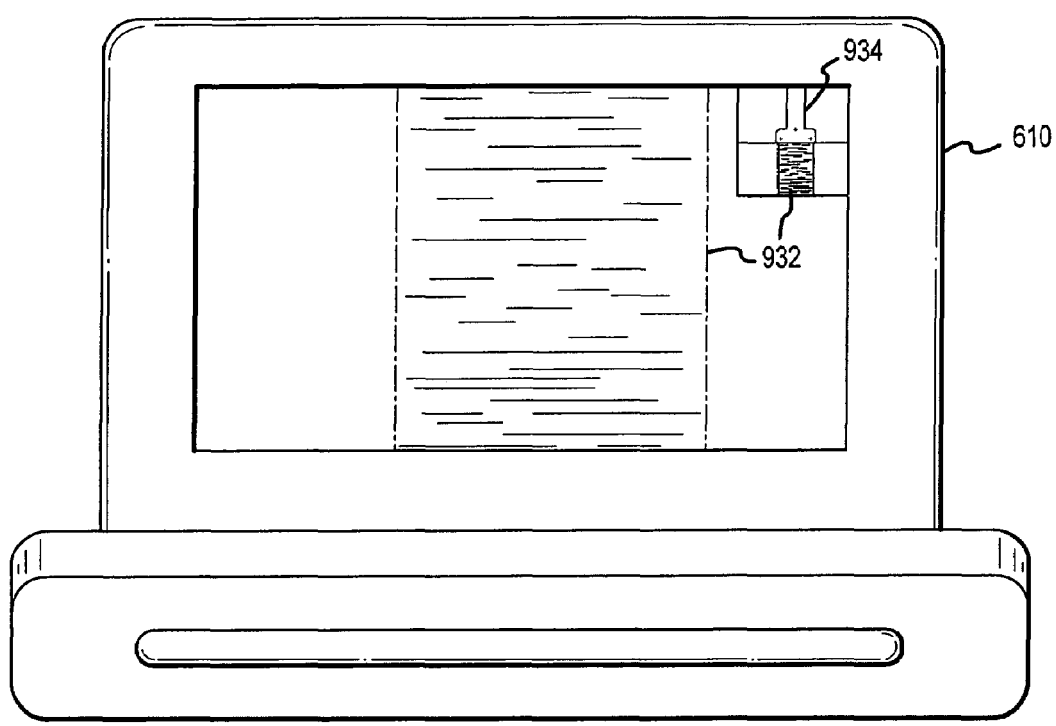
FIG. 9 illustrates yet another exemplary combined image capable of being shown on the display screen in accordance with the present invention.

As illustrated in FIG. 8 and FIG. 9, in accordance with the present invention, control system 600 is also capable of generating various other combined image configurations, such as, split-screen images or "picture-in-picture" images. For example, FIG. 8 illustrates a combined image wherein the combined image comprises the primary image and includes an additional inlay of the transducer image 832 comprising a secondary image. Further, with reference to FIG. 9, a combined image is illustrated that includes the transducer image 932 being central to the display device 912 screen as a primary image, and a secondary image being included wherein the secondary image represents the combined transducer image 932 and positional image 934 as the secondary image. It should be noted that other variations of the images, including different sizes, locations or types, such as two-dimensional or three-dimensional images, can be suitably displayed in accordance with various other embodiments of the present invention.

As a result of the imaging information provided, medical practitioners can utilize the information to facilitate the treatment and diagnosis of their patients. In addition, the information can be utilized in various manners. For example, as the medical treatment and diagnosis system is utilized and imaging information is being observed, a medical practitioner can obtain a real-time assessment of the correlation between the position and/or orientation of the transducer and the imaging, temperature or therapeutic effects provided by the transducer for the treatment region. Accordingly, the medical practitioner can utilize the system to guide the transducer to desirable positions on the patient's surface to obtain the desired treatment or imaging information.

In addition, as the information is received, the control system can suitably store the imaging information in a database for later use and retrieval. For example, it is often difficult when treating patients on subsequent visits to repeat the ultrasonic treatment, imaging, or measurements obtained from prior visits. However, through use of the medical treatment and diagnosis system of the present invention, medical practitioners can realize repeatability and consistency in their treatment of previous patients.

Moreover, the information captured and stored by the control system can also be utilized as a guidance tool with respect to new or different patients. For example, if a particular position on a patient, for example, a fixed distance from a patient reference point, yields favorable or desired results, medical practitioners can utilize the system to suitably re-position the transducer to the ideal or desired position for obtaining similar results. Further, the system can be utilized to train medical practitioners as to the most suitable positions for the transducer depending on the medical operation to be performed. For example, a video stream demonstrating 10 to 15 seconds of operation of a transducer through display of a combined image can demonstrate appropriate techniques for scanning of a treatment region.

In addition to storing the information, the control system can also be configured to process the information, such as through various algorithms and the like, to further improve the treatment process. For example, various artificial intelligence and other system learning functions can be implemented to provide an ever-improving system for facilitating treatment of patients.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the visual imaging system is described above is suitably for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

We claim:

1. A non-invasive treatment and imaging system comprising:
   a control system configured for control of said non-invasive treatment and imaging system;
   an extracorporeal probe assembly configured for treatment of a patient, said probe assembly comprising a transducer configured for obtaining patient information and for facilitating treatment of the patient; and
   an imaging device configured for capturing positional information of said transducer with respect to a patient, said imaging device being directly attached to said transducer to move along with said transducer and to facilitate tracking any movement of said transducer.

2. A system according to claim 1, wherein said control system is configured for assessing the patient information and the positional information to facilitate use of said transducer at a desired position with respect to the patient.

3. A system according to claim 1, wherein said transducer comprises an ultrasonic transducer, said ultrasonic transducer being adapted to transmit imaging information comprising ultrasonic images of a treatment region of the patient to said control system.

4. A system according to claim 3, wherein said control system further comprises a central processing unit, said central processing unit comprising an algorithm configured for processing the imaging information and the positional information.

5. A system according to claim 4, wherein said control system further comprises a memory unit for storing the imaging information and the positional information.

6. A system according to claim 4, wherein said control system further comprises a display unit for displaying the imaging information and the positional information.

7. A system according to claim 6, wherein the positional information is combined via said algorithm within said control system with at least one of an acoustic image, a thermal image, and a therapy treatment image to provide a combined image.

8. A system according to claim 6, wherein the positional information is combined via said algorithm and said control system with the imaging information to provide a fused image.

9. A system according to claim 8, wherein said fused image comprises the positional information configured to display a position of said transducer relative to the patient in fusion with the imaging information configured to display an ultrasonic image of a treatment region.

10. A system according to claim 9, wherein said fused image provides an image similar to a cross-sectional view of the patient and the treatment region.

11. A system according to claim 9, wherein said display unit is configured to display a primary image comprising said fused image, and is configured to display a secondary image comprising one of the positional information configured to display the position of said transducer relative to the patient and the imaging information configured to display the ultrasonic image of the treatment region.

12. A system according to claim 8, wherein said probe assembly comprises a positioning indicator configured with said transducer, said positioning indicator configured to permit said control system to correlate a geometry position of said transducer with respect to the patient to a geometry of an ultrasonic image of a treatment region of the patient.

13. A system according to claim 12, wherein said positioning indicator facilitates scaling of the fused image during changes in position of said transducer.

14. A system according to claim 12, wherein said positioning indicator comprises a series of triangulation marks.

15. A system according to claim 12, wherein said positioning indicator comprises at least one of an electromagnetic device and a gravitational accelerometer.

16. A system according to claim 1, wherein said transducer comprises at least one of an acoustic, therapy and treatment monitoring transducer and is configured for transmitting said patient information to said control system.

17. A system according to claim 1, wherein said transducer comprises a combined ultrasonic imaging, therapy and temperature monitoring transducer and is configured for transmitting said patient information to said control system.

18. A system according to claim 1, wherein said imaging device comprises a video camera configured for sending a video stream to said control system, said video stream correlative of the positional information of said transducer during treatment.

19. A system according to claim 1, wherein said probe assembly further comprises an arm member connecting said imaging device to a housing of said transducer in a fixed position relative to said transducer, said arm member being configured to facilitate the capturing of positional information by said imaging device of said transducer during operation.

20. A system according to claim 19, wherein said probe assembly further comprises an attachment device for attaching said arm member to the housing of said transducer.

21. A non-invasive treatment and imaging system, said system comprising:
an extracorporeal probe assembly configured for treatment of a patient, said extracorporeal probe assembly comprising an ultrasonic transducer, said ultrasonic transducer being adapted to send imaging information comprising ultrasonic images of a treatment region of the patient for facilitating treatment of the patient; and
an imaging device configured for capturing positional information of said transducer with respect to a patient during operation, said imaging device being configured for physical attachment to said transducer during operation to facilitate tracking of movement of said transducer, said imaging device and said transducer separated by a fixed distance and configured to move substantially in unison.

22. A system according to claim 21, wherein said non-invasive treatment and imaging system is configured to permit a control system to assess the positional information to facilitate use of said transducer at a desired position with respect to the patient.

23. A system according to claim 21, wherein said transducer comprises a combined ultrasonic imaging, therapy and temperature monitoring transducer and is configured for transmitting patient information to a control system.

24. A system according to claim 21, wherein said probe assembly further comprises an arm member connecting said imaging device to a housing of said transducer, said arm member being configured to facilitate the capturing of positional information of said transducer during operation.

25. A system according to claim 24, wherein said arm member comprises an adjustable device which can position said imaging device in a plurality of fixed positions with respect to said transducer to provide a plurality of views of said transducer with respect to the patient.

26. A system according to claim 24, wherein said arm member comprises a substantially rigid member which can position said imaging device in a substantially permanent position with respect to said transducer to provide a fixed view of said transducer with respect to a patient.

27. A system according to claim 24, wherein said arm member is integrated directly into the housing of said transducer.

28. A system according to claim 24, wherein said probe assembly further comprises an attachment device for attaching said arm member to the housing of said transducer.

29. A system according to claim 28, wherein said attachment device comprises a clip configured to securely attach said arm member to the housing of said transducer, said clip having an inner contour shaped to an outer contour of the housing of said transducer such that once said clip is attached to said transducer, said imaging device can follow in a direct correlation to movement and position of said transducer.

30. A system according to claim 21, wherein said probe assembly further comprises a positioning indicator configured to provide geometric information regarding the positional information of said transducer during operation.

31. A system according to claim 30, wherein said imaging information and said positional information are combined to provide a fused image.

32. A system according to claim 31, wherein said fused image comprises the positional information configured to display a position of said transducer relative to the patient in fusion with the imaging information configured to display an ultrasonic image of treatment region.

33. A system according to claim 32 wherein said fused image is substantially identical to a cross-sectional view of the patient and the treatment region.

34. A system according to claim 31, wherein said positioning indicator facilitates scaling of the fused image during changes in position of said transducer.

35. A non-invasive treatment and imaging system comprising:
a control system configured for operation of said treatment and imaging system;
an extracorporeal probe assembly configured for facilitating non-invasive treatment of a patient, said probe assembly comprising a transducer configured for obtaining imaging information and delivering ultrasound energy to said patient for treatment; and
an imaging device configured for capturing orientation information of said transducer with respect to the patient, said imaging device being rigidly attached to said transducer during positioning of said transducer such that a spatial relationship between said imaging device and said probe remains substantially fixed.

36. The treatment and imaging system according to claim 35, wherein said control system is configured for assessing said imaging information and said orientation information to facilitate use of said transducer at a desired position with respect to the patient.

37. The treatment and imaging system according to claim 35, wherein said orientation information is combined with said imaging information via an algorithm within said control system to provide a fused image.

38. The treatment and imaging system according to claim 37, wherein said display unit is configured to display a primary image comprising said fused image, and is configured to display a secondary image comprising one of said orientation information and said imaging information.

39. The treatment and imaging system according to claim 35, wherein said transducer comprises a positioning indicator configured to facilitate said control system in correlating orientation of said transducer with respect to the patient.

40. The treatment and imaging system according to claim 39, wherein said positioning indicator comprises a series of triangulation marks.

41. A system for use in providing non-invasive treatment of a patient, said system comprising:
non-invasive probe assembly comprising an ultrasonic transducer adapted to obtain imaging information of a treatment region of the patient and to deliver ultrasonic energy to the treatment region for treatment;
a positioning device configured for capturing positional information of said transducer with respect to the patient, wherein said positioning device is connected to said transducer through an arm member comprising a substantially rigid member which can position said positioning device in a plurality of substantially fixed positions with respect to said transducer; and
said positioning device being physically attached in a fixed position relative to said transducer during positioning of said transducer, and wherein said positional information and said imaging information are combined on a real-time basis.

42. The system according to claim 41, wherein said transducer further comprises a positioning indicator configured to facilitate capturing geometric information from said transducer during operation.

43. The system according to claim 41, further comprising an imaging device, wherein said imaging device comprises a conventional device capable of capturing visual information relating to the position of said transducer.

* * * * *